Figure 1:
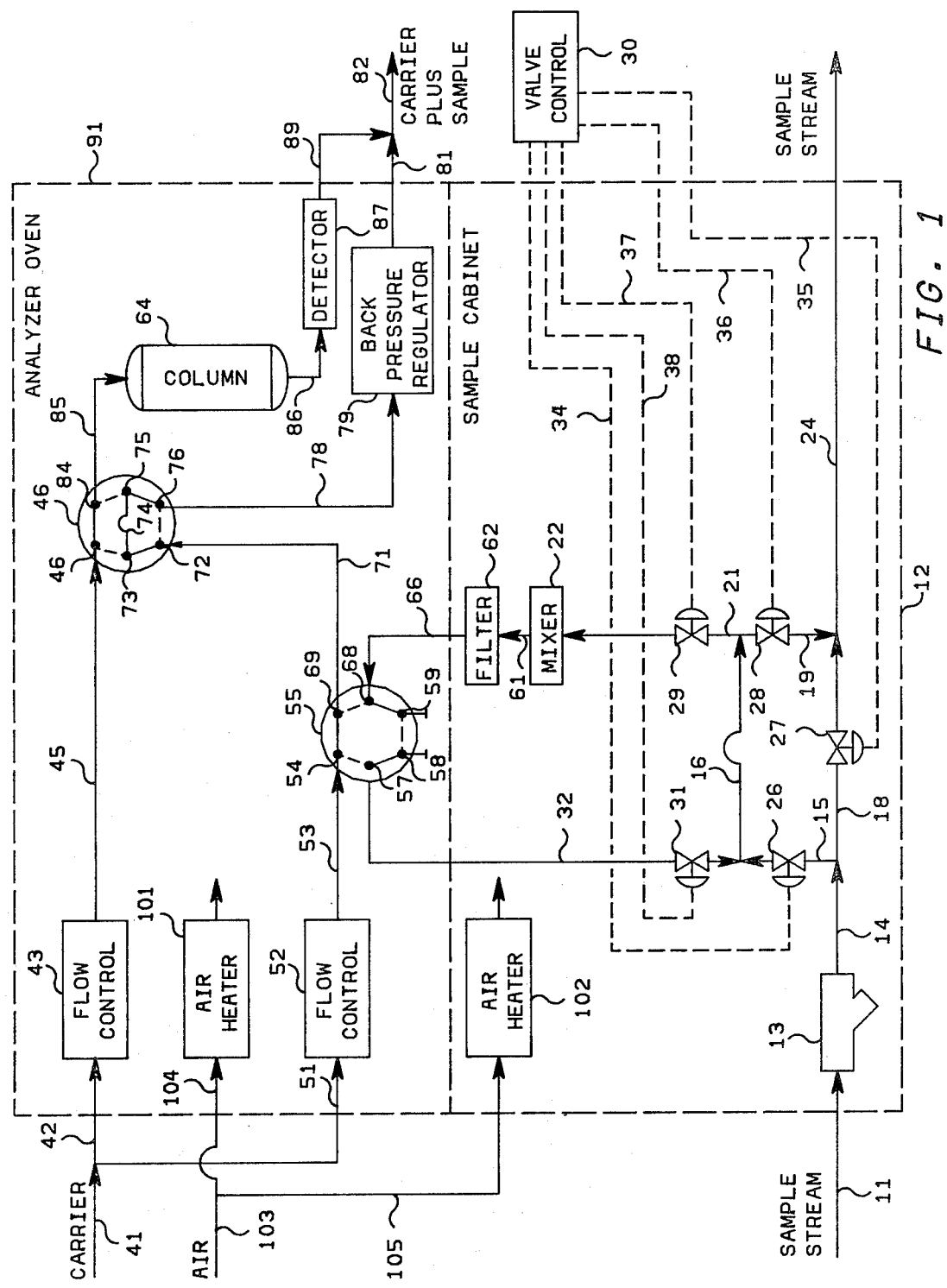

United States Patent [19]

Roof

[11] 4,271,703
[45] Jun. 9, 1981

[54] HIGH TEMPERATURE SAMPLING SYSTEM FOR LIQUID CHROMATOGRAPHY

[75] Inventor: Lewis B. Roof, Bartlesville, Okla.

[73] Assignee: Phillips Petroleum Company, Bartlesville, Okla.

[21] Appl. No.: 81,608

[22] Filed: Oct. 3, 1979

[51] Int. Cl.³ .............................................. G01N 1/10
[52] U.S. Cl. ............................... 73/863.11; 73/864.83
[58] Field of Search ...... 73/422 GC, 421 TC, 61.1 C, 73/23.1

[56] References Cited

U.S. PATENT DOCUMENTS

| 3,198,001 | 8/1965 | Ferrin .................................. 73/23.1 |
| 3,438,261 | 4/1969 | Collins, Jr. . |
| 3,506,640 | 4/1970 | Reid et al. . |
| 4,070,913 | 1/1978 | Roof . |
| 4,186,607 | 2/1980 | Porter et al. .................. 73/422 GC |

Primary Examiner—S. Clement Swisher

[57] ABSTRACT

A high temperature sampling system is provided for obtaining a sample to be analyzed by liquid chromatography. A sample of a liquid to be analyzed, which is at an elevated temperature, is obtained by utilizing a plurality of valves to fill a sample conduit in a hot zone. The thus obtained sample is diluted and is then provided to a chromatographic analyzer sample valve which is located in a cooler zone. In this manner, samples of liquids are obtainable at temperatures substantially above those temperatures which can be withstood by a chromatographic analyzer sample valve.

20 Claims, 1 Drawing Figure

HIGH TEMPERATURE SAMPLING SYSTEM FOR LIQUID CHROMATOGRAPHY

This invention relates to liquid chromatography. In one aspect this invention relates to method and apparatus for obtaining samples, at elevated temperatures, for analysis by liquid chromatography.

A chromatographic analyzer is an analytical instrument that is used to separate in time and individually detect the constituents of a sample to be analyzed. The chromatographic analyzer typically includes an analytical column through which a carrier fluid is passed continuously. A chromatographic analyzer sample valve is typically utilized to inject the sample to be analyzed into the carrier stream and the sample is thus carried through the analytical column. Sample constituents are carried through the analytical column at different velocities and in this manner the sample constituents are separated in time.

A detector is employed to detect the separated constituents and the detector output signal typically is plotted as a function of time to produce what is termed a chromatogram. As each sample component is eluted from the column, the component produces a sharp increase in the detector output signal amplitude, which increase appears as a peak or spike in the chromatogram.

Liquid chromatography has become increasingly important for use in the analysis of process streams in chemical manufacturing processes and also for use in the analysis of other liquid streams. One limitation which has been present in liquid chromatography is the temperature of the process stream which can be analyzed. Typical chromatographic analyzer sample valves will not withstand a temperature greater than about 400° F. Many materials, such as polymers, have melting temperatures substantially above 400° F. and it is sometimes desirable to analyze these molten fluid streams.

It is thus an object of this invention to provide method and apparatus for obtaining samples, at temperatures above those which can be withstood by typical chromatographic analyzer sample valves, for analysis by liquid chromatography.

In accordance with the present invention, method and apparatus is provided whereby a plurality of control valves and a sample conduit are utilized to obtain a sample from a liquid stream which is at an elevated temperature. The thus obtained sample is then diluted in a solvent for the sample liquid. The sample conduit, control valves and diluter are located in a sample cabinet which is maintained at an elevated temperature substantially equal to the temperature of the liquid stream.

After dilution, the sample is provided to a chromatographic analyzer sample valve which is located in an analyzer oven maintained at a substantially lower temperature. The diluted sample will cool substantially prior to entering the chromatographic analyzer sample valve located in the analyzer oven. However, because the sample has been diluted it will remain in a fluid state even though the temperature of the analyzer oven is below the melting point of the polymeric component which makes up the liquid stream.

The diluted sample is provided through the first chromatographic analyzer sample valve to a second chromatographic analyzer sample valve which provides a sample of the diluted stream to the chromatographic analyzer column. In this manner, an analysis of a fluid stream which is at an elevated temperature which could not be withstood by a typical chromatographic analyzer sample valve may be obtained.

Other objects and advantages of the invention will be apparent from the foregoing brief description of the invention and the appended claims as well as the detailed description of the drawing in which:

FIG. 1 is a diagrammatic representation of a liquid chromatography system together with apparatus for obtaining a sample of a liquid stream which is at an elevated temperature.

The invention is described in terms of a particular configuration of a liquid chromatograph system and in terms of a particular sampling apparatus configuration. However, the invention is applicable to any apparatus configuration which accomplishes the purpose of the present invention. The invention is also described in terms of pneumatic control valve but is applicable to any type of control valve which can be remotely actuated.

Referring now to FIG. 1, a liquid at an elevated temperature flows through conduit means 11 into the sample cabinet 12. The sample cabinet 12 will preferably be maintained at a temperature substantially equal to the temperature of the liquid stream, typically a process stream, flowing through conduit means 11. The temperature of the liquid stream will typically be above 400° F. However, the invention is applicable to lower temperatures if it is not desired to maintain the chromatographic analyzer sample valves in the lower temperature. The liquid stream flowing through conduit means 11 is preferably filtered by the filter 13 and is then provided through the combination of conduit means 14 and 15 to the sample conduit 16. From the sample conduit 16, the liquid may flow through conduit means 21 to the mixer 22 or may flow through the combination of conduit means 19 and 24 out of the sample cabinet 12. The liquid stream may also flow through the combination of conduit means 14, 18 and 24 out of the sample cabinet 12. The flow of the liquid stream is directed by the pneumatic control valves 26–29 which are operably located in conduit means 15, 18, 19 and 21, respectively.

Any suitable control system may be utilized to open and close the pneumatic control valves 26–29 and 31. The valve control 30 illustrated in the FIGURE is preferably a means for supplying pressure to the pneumatic control valves 26–29 and 31 if it is desired to open any one of the pneumatic control valves 26–29 and 31. Valve control 30 is connected through conduit means 34–38 to pneumatic control valves 26–29 and 31, respectively.

When it is desired to fill the sample conduit 16 with the liquid flowing through conduit means 11, pneumatic control valve 27 is closed and both pneumatic control valve 26 and 28 are opened. Pneumatic control valve 29 is closed and pneumatic control valve 31 which is operably located in conduit means 32 is closed. Liquid thus flows through the combination of conduit means 11, 14, and 15 to the sample conduit 16. From the sample conduit 16, the liquid flows through conduit means 19 and 24 out of the sample cabinet 12.

After a smooth flow has been established, pneumatic control valves 26 and 28 are closed and pneumatic control valve 27 is opened. The liquid to be analyzed will thus flow through the combination of conduit means 14, 18 and 24 out of the sample cabinet 12. However, the sample conduit 16 will remain filled with a sample of the liquid to be analyzed.

A suitable carrier fluid which will dissolve the substance flowing through conduit means 11 is provided through conduit means 41 and 42 to the flow control 43. The flow control 43 may be any suitable flow control for liquid chromatography but will generally be a piece of capillary tubing. From the flow control 43, the carrier fluid is provided through conduit means 45 to port 46 of the chromatographic analyzer sample valve 47.

In like manner, the carrier fluid flowing through conduit means 41 is provided through the combination of conduit means 41 and conduit means 51 to the flow control 52. The flow control 52 will typically be substantially identical to the flow control 43. From the flow control 52, the carrier fluid is provided through conduit means 53 to port 54 of the chromatographic analyzer sample valve 55.

The sample valves 47 and 55 are essentially two-position valves which are preferably the Model 8 sample valves manufactured by Applied Automation, Inc., Bartlesville, Ok. The solid lines between the ports of the sample valves indicates the flow in the first position. The dotted lines between the sample ports of the sample valves 47 and 55 indicates the flow in the second position. It is noted that the sample valve 55 does not contain a sample loop.

When it is desired to force the liquid which has been trapped in the sample conduit 16 from the sample conduit 16 into the mixer 22, the sample valve 55 is switched to the second position and pneumatic control valves 31 and 29 are opened. Carrier fluid flows from port 54 to port 57 of the sample valve 55 and is thus provided through conduit means 32 to the sample conduit 16. It is noted that both ports 58 and 59 of the sample valve 55 are plugged. The liquid in the sample conduit 16 is thus forced from the sample conduit 16 through conduit means 21 into the mixer 22. The mixer 22 may be any suitable mixer but is preferably a magnetic stirrer type mixer.

It is noted that the presence of pneumatic control valves 29 and 31 is required only if the carrier fluid boils or flashes at the temperature of the sample cabinet and pressure of the sample stream. When the carrier fluid is being utilized to force the sample out of the sample loop, the carrier fluid is subjected to the pressure on the carrier flowing through conduit means 41. This pressure will be sufficient to prevent the carrier from flashing at the temperature in the sample cabinet. However, when the chromatographic analyzer sample valve 55 is switched to the first position, the carrier fluid remaining in the sample cabinet will be subjected to the pressure of the sample stream if pneumatic control valves 26 and 28 were opened and pneumatic control valves 29 and 31 were not present. For many carrier/sample systems, the carrier fluid remaining in the sample cabinet would flash at the pressure of the sample stream which will generally be substantially lower than the carrier pressure. This is totally undesirable. Thus, pneumatic control valves 29 and 31 are required if the carrier fluid boils or flashes at the temperature of the sample cabinet and pressure of the sample stream. If the carrier fluid does not boil or flash at the temperature of the sample cabinet and pressure of the sample stream then pneumatic control valves 29 and 31 are not required.

After the liquid to be analyzed has been diluted with the carrier fluid in the mixer 22, the thus diluted solution is provided through conduit means 61 to the filter 62 which removes particles which would have a tendency to plug the chromatographic column 64 or the sample valves 47 and 55. From the filter 62, the diluted solution is provided through conduit means 66 to port 68 of the sample valve 55. With the sample valve 55 in the second position, the diluted solution is provided to port 69 of the sample valve 55 and it is thus provided through conduit means 71 to port 72 of the sample valve 47. With the sample valve 47 in the first position, the diluted sample flows to port 73. The diluted sample flows from port 73 through the sample loop 74 to port 75 and from port 75 to port 76 of the sample valve 47. From port 76 the diluted sample flows through conduit means 78 through the back-pressure regulator 79 and is removed from the analyzer oven through the combination of conduit means 81 and 82. The back-pressure regulator may be set at any desired pressure. Preferably, the back-pressure regulator is set at a pressure which will prevent flashing of the carrier in the sample cabinet 12.

When it is desired to supply a sample to the chromatographic column 64, the sample valve 47 is switched to the second position. The carrier fluid flowing through conduit means 45 flows from port 46 to port 73 of the sample valve 47. The sample in the sample loop 74 is forced out of the sample loop 74 and flows from port 75 to port 84 of the sample valve 47. From port 84 the carrier plus sample is provided through conduit means 85 to the chromatographic column 64. The eluted components flow from the chromatographic column 64 through conduit means 86 and are provided to the sample side of the detector 87. The detector 87 may be any suitable detector for liquid chromatography. Detectors such as refractive index detectors and dielectric constant detectors are commonly utilized. The manner in which a chromatographic analyzer detector operates to provide output signals which are representative of the concentration of eluted components from the chromatographic column 14 is well known. The effluent from the chromatographic column 64 flows through the detector 87 and is vented from the analyzer oven 91 through the combination of conduit means 89 and 82.

Temperature control of the analyzer oven 91 and the sample cabinet 12 is accomplished by means of the air heaters 101 and 102, respectively. Air is supplied to the air heater 101 through the combination of conduit means 103 and 104. Air is supplied to the air heater 102 through the combination of conduit means 103 and 105. The air heaters 101 and 102 are controlled in a conventional manner to maintain desired temperatures in the analyzer oven 91 and the sample cabinet 12.

As has been previously stated, the primary function of the present invention is to obtain a sample from a liquid stream which is at an elevated temperature. Once the sample is obtained, liquid chromatography is utilized to analyze the sample. The sample valves 47 and 55 will generally withstand temperatures of up to about 400° F. Since many process streams may have temperatures above 400° F., it is critical that the sample valves 47 and 55 be isolated from the high temperature of the sample cabinet which is typically maintained at a temperature substantially equal to the temperature of the liquid to be analyzed. This is accomplished by placing the sample valves 47 and 55 in the analyzer oven and placing only the pneumatic control valves 26–29 and 31, the mixer 22, and the filters 13 and 62 in the hot zone of the sample cabinet 12. The temperature of liquids which can be sampled by the sample system of the present invention will typically be limited by the temperature limitation on the pneumatic control valves. Pneumatic control valves are presently available from Autoclave Engineers, Erie, Pa. which will operate up to about 1200° F. However, if pneumatic control valves, or other types of control valves which can be remotely actuated, can be obtained which will operate above 1200° F., the invention is applicable to obtaining samples from liquid streams having even higher temperatures than 1200° F. With present commercially available sample valves and control valves, it can be seen that the present invention provides an improvement of 800° F. in the temperature range of process streams which can be analyzed by liquid chromatography.

The invention has been described in terms of a preferred embodiment as illustrated in the FIGURE. Although the invention has been illustrated in terms of a preferred embodiment, reasonable variations and modifications are possible by those skilled in the art within the scope of the described invention and the appended claims.

That which is claimed is:

1. Apparatus for obtaining a sample of a hot liquid for analysis by liquid chromatography comprising:
    a sample conduit means having first and second ends;
    a first conduit means for supplying said hot liquid to the first end of said sample conduit means;
    a first control valve means operably located in said first conduit means;
    a second conduit means for removing said hot liquid from the second end of said sample conduit means;
    a second control valve means operably located in said second conduit means;
    a third conduit means for supplying a carrier fluid, which is a solvent for said hot liquid, to the first end of said sample conduit means;
    a third control valve means operably located in said third conduit means;
    a diluter means;
    a fourth conduit means for supplying said hot liquid and said carrier fluid from the second end of said sample conduit means to said diluter means;
    a fourth control valve means operably located in said fourth conduit means;
    a chromatographic column means;
    means for supplying diluted liquid from said diluter means to said chromatographic column means;
    means for maintaining said chromatographic column means and said means for supplying diluted liquid from said diluter means to said chromatographic column means at a lower temperature than said first, second, third and fourth control valve means, said diluter means, said sample conduit means and at least a portion of said first, second, third and fourth conduit means; and
    means for positioning said first and second control valve means in an open position and said third and fourth control valve means in a closed position when it is desired to fill said sample conduit means with said hot liquid, and for positioning said first and second control valve means in a closed position and said third and fourth control valve means in an open position when it is desired to supply the hot liquid in said sample conduit means and said carrier fluid to said diluter means.

2. Apparatus in accordance with claim 1 additionally comprising:
    a sample valve means having at least first, second, third and fourth ports, said first and fourth ports being in fluid communication with each other when said sample valve means is in a first position, said first and second ports being in fluid communication with each other and said third and fourth ports being in fluid communication with each other when said sample valve means is in a second position; and
    means for supplying said carrier fluid to said first port of said sample valve means, said carrier fluid being supplied from said second port of said sample valve means through said third conduit means to the first end of said sample conduit means when said sample valve means is in the second position.

3. Apparatus in accordance with claim 1 wherein said means for supplying said diluted liquid from said diluter means to said chromatographic column means comprises:
    a first sample valve means having at least first, second, third and fourth ports, said first and fourth ports being in fluid communication with each other when said first sample valve means is in a first position, said first and second ports being in fluid communication with each other and said third and fourth ports being in fluid communication with each other when said first sample valve means is in a second position;
    a second sample valve means having at least first, second, third, fourth, fifth and sixth ports, said first and sixth ports being in fluid communication with each other, said second and third ports being in fluid communication with each other and said fourth and fifth ports being in fluid communication with each other when said second sample valve means is in a first position and said first and second ports being in fluid communication with each other, said third and fourth ports being in fluid communication with each other and said fifth and sixth ports being in fluid communication with each other when said sample valve means is in a second position, said second and fifth ports being connected to each other through a sample loop;
    fifth conduit means for supplying said carrier fluid to the first port of said second sample valve means;
    sixth conduit means for supplying said diluted liquid from said diluter means to the third port of said first sample valve means;
    seventh conduit means for supplying fluid from the fourth port of said first sample valve means to the third port of said second sample valve means;
    eighth conduit means for supplying fluid from the sixth port of said second sample valve means to the inlet of said chromatographic column means, said diluted liquid being supplied from the fourth port of said first sample valve means through said seventh conduit means to the third port of said second sample valve means when said first sample valve means is in said second position, said diluted liquid being supplied to said sample loop of said second sample valve means when said second sample valve means is in said first position, the portion of said diluted liquid in said sample loop of said second sample valve means being supplied to said chromatographic column means when said second sample valve means is in said second position.

4. Apparatus in accordance with claim 3 additionally comprising:

a first filter means operably located in said first conduit means; and a second filter means operably located in said sixth conduit means.

5. Apparatus for obtaining a sample of a hot liquid for analysis by liquid chromatography comprising:
   a sample conduit means having first and second ends;
   a first conduit means for supplying said hot liquid to the first end of said sample conduit means;
   a first control valve means operably located in said first conduit means;
   a second conduit means for removing said hot liquid from the second end of said sample conduit means;
   a second control valve means operably located in said second conduit means;
   a third conduit means for supplying a carrier fluid, which is a solvent for said hot liquid and which does not boil at a temperature substantially equal to the temperature of said hot liquid and a pressure substantially equal to the pressure of said hot liquid, to the first end of said sample conduit means;
   a diluter means;
   a fourth conduit means for supplying said hot liquid and said carrier fluid from the second end of said sample conduit means to said diluter means;
   a chromatographic column means;
   means for supplying diluted liquid from said diluter means to said chromatographic column means;
   means for maintaining said chromatographic column means and said means for supplying diluted liquid from said diluter means to said chromatographic column means at a lower temperature than said first and second control valve means, said diluter means, said sample conduit means and at least a portion of said first, second, third and fourth conduit means; and
   means for positioning said first and second control valve means in an open position when it is desired to fill said sample conduit means with said hot liquid, and for positioning said first and second control valve means in a closed position when it is desired to supply the hot liquid in said sample conduit means and said carrier fluid to said diluter means.

6. Apparatus in accordance with claim 5 additionally comprising:
   a sample valve means having at least first, second, third and fourth ports, said first and fourth ports being in fluid communication with each other when said sample valve means is in a first position, said first and second ports being in fluid communication with each other and said third and fourth ports being in fluid communication with each other when said sample valve means is in a second position; and
   means for supplying said carrier fluid to said first port of said sample valve means, said carrier fluid being supplied from said second port of said sample valve means through said third conduit means to the first end of said sample conduit means when said sample valve means is in the second position.

7. Apparatus in accordance with claim 5 wherein said means for supplying said diluted liquid from said diluter means to said chromatographic column means comprises:
   a first sample valve means having at least first, second, third and fourth ports, said first and fourth ports being in fluid communication with each other when said first sample valve means is in a first position, said first and second ports being in fluid communication with each other and said third and fourth ports being in fluid communication with each other when said first sample valve means is in a second position;
   a second sample valve means having at least first, second, third, fourth, fifth and sixth ports, said first and sixth ports being in fluid communication with each other, said second and third ports being in fluid communication with each other and said fourth and fifth ports being in fluid communication with each other when said second sample valve means is in a first position and said first and second ports being in fluid communication with each other, said third and fourth ports being in fluid communication with each other and said fifth and sixth ports being in fluid communication with each other when said sample valve means is in a second position, said second and fifth ports being connected through a sample loop;
   fifth conduit means for supplying said carrier fluid to the first port of said second sample valve means;
   sixth conduit means for supplying said diluted fluid from said diluter means to the third port of said first sample valve means;
   seventh conduit means for supplying fluid from the fourth port of said first sample valve means to the third port of said second sample valve means;
   eighth conduit means for supplying fluid from the sixth port of said second sample valve means to the inlet of said chromatographic column means, said diluted liquid being supplied from the fourth port of said first sample valve means through said seventh conduit means to the third port of said second sample valve means when said first sample valve means is in said second position, said diluted liquid being supplied to said sample loop of said second sample valve means when said second sample valve means is in said first position, the portion of said diluted liquid in said sample loop of said second sample valve means being supplied to said chromatographic column means when said second sample valve means is in said second position.

8. Apparatus in accordance with claim 7 additionally comprising:
   a first filter means operably located in said first conduit means; and
   a second filter means operably located in said sixth conduit means.

9. A method for obtaining a sample of hot liquid for analysis by liquid chromatography comprising the steps of:
   filling a sample conduit means with said hot liquid;
   isolating said sample conduit means from the source of said hot liquid;
   supplying carrier fluid, which is a solvent for said hot liquid, to said sample conduit means to force the portion of said hot liquid in said sample conduit means out of said sample conduit means;
   mixing said carrier fluid and said hot liquid from said sample conduit means to dilute said hot liquid;
   cooling the thus diluted liquid; and
   chromatographically analyzing the thus cooled diluted liquid.

10. A method in accordance with claim 9 wherein said hot liquid has a temperature in the range of about 400° F. to about 1200° F.

11. A method for obtaining a sample of a hot liquid for analysis by liquid chromatography comprising the steps of:

filling a sample conduit means with said hot liquid;

isolating said sample conduit means from the source of said hot liquid;

actuating a first sample valve means to supply carrier fluid, which is a solvent for said hot liquid, to said sample conduit means to force the portion of said hot liquid in said sample conduit means out of said sample conduit means;

mixing said carrier fluid and said hot liquid to dilute said hot liquid;

cooling the thus diluted liquid;

supplying the thus cooled diluted liquid through the actuated first sample valve means to the sample loop of a second sample valve means; and actuating said second sample valve means to supply the portion of said cooled diluted liquid in said sample loop of said second sample valve means to a chromatographic column, said first sample valve means, said second sample valve means and said chromatographic column being maintained at a temperature less than the temperature of said hot liquid.

12. A method in accordance with claim 11 wherein said hot liquid has a temperature in the range of about 400° F. to about 1200° F.

13. A method in accordance with claim 12 wherein said hot liquid is filtered prior to being supplied to said sample conduit means.

14. A method in accordance with claim 13 wherein said diluted liquid is filtered prior to cooling.

15. A method in accordance with claim 14 wherein said carrier fluid is utilized to force the portion of said cooled diluted sample in said sample loop of said second sample valve means out of said sample loop into said chromatographic column.

16. A method for chromatographically analyzing a polymer which has a melting point greater than the operating temperature of a chromatographic analyzer sample valve comprising the steps of:

filling a sample conduit means with said polymer;

isolating said sample conduit means from the source of said polymer;

actuating a first sample valve means to supply carrier fluid, which is a solvent for said polymer, to said sample conduit means to force the portion of said polymer in said sample conduit means out of said sample conduit means;

mixing said carrier fluid and said polymer to dilute said polymer;

cooling the thus diluted polymer;

supplying the thus cooled diluted polymer through the actuated first sample valve means to the sample loop of a second sample valve means; and actuating said second sample valve means to supply the portion of said cooled diluted polymer in said sample loop of said second sample valve means to a chromatographic column, said first sample valve means, said second sample valve means and said chromatographic column being maintained at a temperature less than the temperature of said polymer, analysis of the eluents flowing from said chromatographic column providing an analysis of said polymer.

17. A method in accordance with claim 16 wherein said polymer has a temperature in the range of about 400° F. to about 1200° F.

18. A method in accordance with claim 17 wherein said polymer is filtered prior to being supplied to said sample conduit means.

19. A method in accordance with claim 18 wherein said polymer is filtered prior to cooling.

20. A method in accordance with claim 19 wherein said carrier fluid is utilized to force the portion of said cooled diluted polymer in said sample loop of said second sample valve means out of said sample loop into said chromatographic column.

* * * * *